United States Patent [19]

Wessel et al.

[11] 3,948,081

[45] Apr. 6, 1976

[54] EXHAUST GAS OPERATED APPARATUS FOR CONTINUOUSLY MEASURING AIR NUMBER OF ENGINE INTAKE MIXTURE

[75] Inventors: Wolf Wessel, Schwieberdingen; Ernst Linder, Muhlacker; Helmut Maurer, Schwieberdingen; Horst Neidhard, Korntal, all of Germany

[73] Assignee: Robert Bosch G.m.b.H., Stuttgart, Germany

[22] Filed: Aug. 9, 1974

[21] Appl. No.: 496,292

[30] Foreign Application Priority Data

Aug. 16, 1973 Germany.......................... 2341422

[52] U.S. Cl. ................................................. 73/23
[51] Int. Cl.² ........................................ G01N 31/04
[58] Field of Search .......... 73/23; 328/143; 307/230

[56] References Cited
UNITED STATES PATENTS

| | | | |
|---|---|---|---|
| 3,220,255 | 11/1965 | Scranton et al...................... | 73/204 |
| 3,611,243 | 10/1971 | Hardtl................................. | 73/23 X |
| 3,644,836 | 2/1972 | Johnson.............................. | 328/143 |
| 3,736,515 | 5/1973 | Kadron et al....................... | 328/143 |
| 3,738,341 | 6/1973 | Loos................................... | 73/231 X |
| 3,820,015 | 6/1974 | Jeunehomme..................... | 73/231 X |

*Primary Examiner*—James J. Gill
*Attorney, Agent, or Firm*—William R. Woodward

[57] ABSTRACT

The output of an oxygen sensor is fed in parallel to the inputs of amplifiers having amplification in different portions of the sensor output range and having different gain. The amplifier outputs are combined in a summing circuit. The result is to smooth out the characteristic of the measurement and to produce a signal that can drive an indicator to provide a meaningful indication in terms of air number. The temperature of the oxygen sensor must be regulated or compensated for for good results.

9 Claims, 3 Drawing Figures

EXHAUST GAS OPERATED APPARATUS FOR CONTINUOUSLY MEASURING AIR NUMBER OF ENGINE INTAKE MIXTURE

Cross reference is made to the following related U.S. patent applications:
U.S. Ser. No. 259,134 — Topp et al.;
U.S. Ser. No. 316,008 — Friese et al.;
U.S. Ser. No. 314,922 — Schmidt et al.;
U.S. Ser. No. 447,475 — Pollner et al.;
U.S. Pat. No. 3782347 — Wessel.

This invention relates to apparatus for continuously measuring the composition of the fuel-air mixture of an internal combustion engine by means of an oxygen sensor located in an exhaust duct of the engine and operatively connected by suitable equipment to an indicating device.

In shop and inspection work it is necessary to set the adjustment controlling the fuel-air mixture of an internal combustion engine at a setting which will result in producing exhaust gas of the lowest possible noxious material content. The composition of the fuel-air mixture supplied to the engine can be expressed by the air number $\lambda$, which is so defined that it has the value 1 when the fuel-air ratio is that of a stoichiometric mixture. When there is excess air, the air number takes values above 1.0, the value being defined by the air-to-fuel ratio by weight. Conversely, when there is an excess of fuel (rich mixture) the air number $\lambda$ is smaller than 1.

It is an object of the invention to provide a measuring apparatus by means of which the composition of the fuel-air mixture supplied to the engine can be continuously determined ($\lambda$ measurement). The equipment should be as simple as possible in its construction and should operate safely and reliably in rough shop operations.

SUBJECT MATTER OF THE PRESENT INVENTION

Briefly, an oxygen sensor in the exhaust system of the engine provides its output in common to a plurality of amplifiers having different amplification factors and constituted so as to amplify over different portions of the range of values which the output of the oxygen sensor may take, each amplifier having a different input threshold, and the outputs of these amplifiers are coupled together to an indicating device by resistors so as to exert a controlled force for actuating the indicating device. When the sensor output is below the input threshold of an amplifier, as determined by a comparison circuit, a diode blocks delivery of the output and also a gain-setting negative feedback path.

The resistor coupling of the aforesaid amplifiers preferably constitutes a summing circuit and the summing circuit may contain a second stage amplifier that drives the indicating device. All of the amplifiers may utilize operational amplifier units and the resistors of the summing circuit may be driven from the respective taps of voltage dividers across the operating voltage of the system of amplifiers, each of these taps being respectively connected to the output of the operational amplifier of one of the first stage amplifiers through a diode. All of the operational amplifiers preferably are provided with feedback resistors to their inverting inputs and in the case of the first stage amplifiers this resistor is connected between the aforesaid voltage divider tap and the inverting input and another diode is provided between the inverting input and the output of the operational amplifier.

One or more of the first stage amplifiers is provided with a temperature compensating component located in the immediate neighborhood of the oxygen sensor and this component is preferably a negative temperature coefficient resistor in series between the output of the oxygen sensor and the inverting input of the operational amplifier of the particular first stage amplifier.

The invention is further described by way of example with reference to the accompanying drawings, in which.

Figure 1:
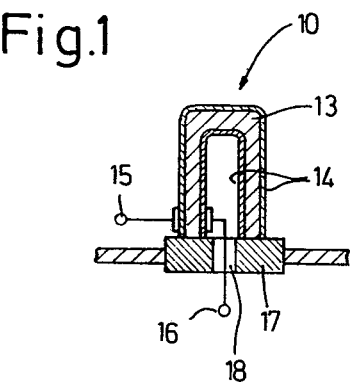
FIG. 1 is a cross-sectional diagram showing the construction of an oxygen sensor.

The constitution of an oxygen sensor 10 is shown schematically in FIG. 1. As indicated diagrammatically in FIG. 3, the oxygen sensor 10 is located in the exhaust manifold 11 of an internal combustion engine. The sensor 10 consists of a small tube 13 closed at one end made of a sintered solid electrolyte. The solid electrolyte 13 is coated on both sides with a vapor deposited porous platinum layer 14. The two platinum layers 14 are provided with contacts connected electrically to the terminals 15 and 16 of the device. The solid electrolyte tube 13 is held in the wall of the exhaust manifold 11 by a mounting 17 in the nature of a bushing. The mounting 17 has a bore 18 through which outside air can penetrate into the internal cavity of the tube 13. The outer surface of the tube 13 is exposed to exhaust gas that streams around it.

Figure 2:
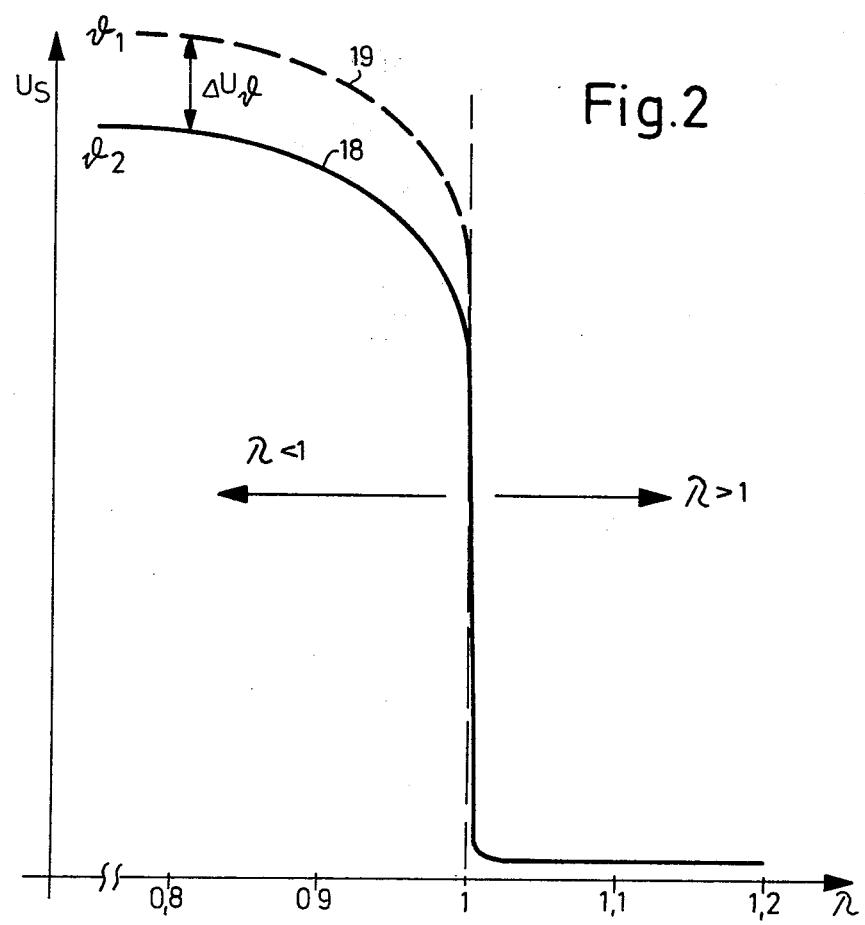
FIG. 2 is a graph plotting the output signal of the oxygen sensor against the air number $\lambda$.

At high temperatures such as are normal for the exhaust gas stream, the solid electrolyte supports the migration of oxygen ions. Zirconium dioxide, for example, can be utilized for this solid electrolyte. To the extent that the oxygen partial pressure of the exhaust gas differs from the oxygen partial pressure of the outside air, a potential difference appears between the electrical terminals 15 and 16 that is shown in FIG. 2 plotted against the air number $\lambda$. The potential difference depends logarithmitically on the quotient of the oxygen partial pressures on the two sides of the solid electrolyte. For this reason, the output voltage of the oxygen sensor 10 shows a marked potential jump in the neighborhood of the air number $\lambda = 1.0$.

In FIG. 2 the output between the terminals 15 and 16 of the oxygen sensor 10 is plotted, as mentioned before, against the air number of the fuel-air mixture supplied to the engine. This graph shows that for low values, from about 0.8 to about 0.98, of the air number $\lambda$ (rich fuel-air mixture), a relatively high output voltage appears between the terminals 15 and 16 that drops gently as the value $\lambda = 0.98$ is approached. In the region between $\lambda = 0.99$ and $\lambda = 1.01$, the voltage between the terminals 15 and 16 changes sharply and in the region where $\lambda > 1.01$, there is a very low output voltage between the terminals 15 and 16 of the oxygen sensor 10. FIG. 2 further shows that the output voltage between the terminals 15 and 16 is strongly dependent upon temperature. The solid line curve 18 holds for lower temperatures and the dashed line curve holds for higher temperatures, typical low and high temperatures having been chosen to show the effect.

In order to provide unambiguous information and indication of the composition of the fuel-air mixture, i.e., to indicate continuously the current value of λ by an indicator device, precautions must be taken to compensate for the temperature dependence of the output signal of the oxygen sensor and also measures must be taken to assure that the steep portion of the curve 18 which coincides with the curve 19 is modified or linearized to provide an unambiguous relation to the air number λ.

Figure 3:
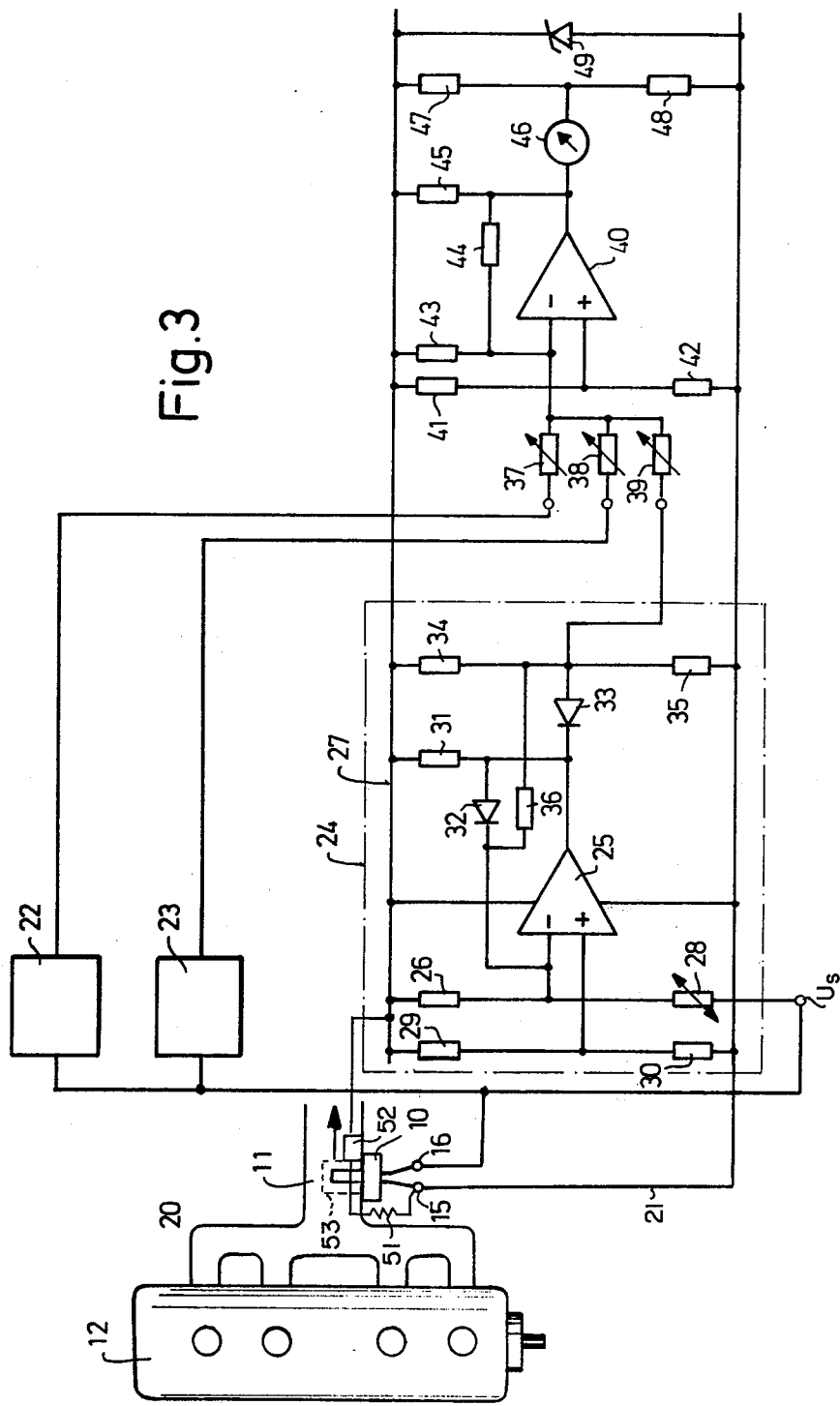
FIG. 3 is a circuit diagram of measuring apparatus for obtaining and indicating the air number $\lambda$.

The circuit shown in FIG. 3 is utilized to linearize the output signal, which is to say to smooth out the irregularities in the direction of the abscissae.

Branch pipes 20 lead from the engine 12 to the exhaust manifold 11 in which the oxygen sensor 10 is located, which delivers an output signal from which the composition of the fuel-air mixture supplied to the engine can be determined. This output signal appears between the terminals 15 and 16 as already mentioned in connection with the description of FIG. 1. The terminal 15 is connected to a common negative bus 21 which is commonly grounded to the chassis in motor vehicles. The inputs of amplifiers 22, 23 and 24 are connected to the output terminal 16 of the oxygen sensor 10. The amplifier 24 is shown in detail in FIG. 3. Its constitution is the same at that of the amplifiers 22 and 23 which are accordingly shown simply in block form. Only the electrical dimensions of certain individual components differ between one and another of these amplifiers.

The amplifier 24 contains an operational amplifier unit 25. The inverting input of this operational amplifier unit is connected through a resistor 26 to the positive supply voltage bus 27. The inverting input of the operational amplifier unit 25 is connected through a negative temperature coefficient resistor 28 to the terminal 16 of the oxygen sensor 10 that supplies the output signal of the oxygen sensor to the amplifier The non-inverting input of the operational amplifier unit 25 is connected to the tap of a voltage divider composed of the resistors 29 and 30 connected between the positive voltage bus 27 and the negative voltage bus 21. The output of the operational amplifier unit 25 is connected through a resistor 31 to the positive voltage bus 27 and through a diode 32 with the inverting input of the operational amplifier unit, and it is further connected over another diode 33 to the tap of a second voltage divider constituted of the resistors 34 and 35 connected between the positive and negative voltage busses. A resistor 36 leads from the tap of the second voltage divider just mentioned to the inverting input of the operational amplifier 25, providing negative feedback. Instead of the diode 33, a transistor can be provided with its base connected to the output of the operational amplifier 25, its emitter with the tap of the voltage divider 34, 35 and its collector with the grounded negative voltage bus 21.

Operation of the Circuit of FIG. 3. So long as the voltage related to the output voltage $U_s$ of the oxygen sensor 10, that appears at the tap of the voltage divider 26, 28 is lower than the fixed bias voltage applied to the non-inverting input of the operational amplifier by means of the voltage divider constituted by the resistors 29 and 30, an output voltage having a positive value is produced at the output of the operational amplifier 25. In consequence, the diode 33 is blocked and the output voltage divider constituted of the resistors 34 and 35 cannot be affected by the amplifier output. The current that is necessary to raise the voltage of the tap of the voltage divider formed by the resistors 26 and 28 to the same value as the bias produced by the voltage divider formed by the resistors 29 and 30 in order to produce the sum voltage 0 between the two inputs of the operational amplifier is supplied over the diode 32 and the load resistor 31.

As the output voltage of the oxygen sensor 10 rises, the threshold value is reached at which the voltage at the tap of the voltage divider formed by the resistors 29 and 30 has the same value as the voltage at the tap of the divider formed by the resistors 26 and 28. No additional current needs then to be fed to the voltage divider formed of the resistors 26 and 28 and, similarly, the current must not be reduced, so that the diodes 32 and 33 block. With only a slight further increase of the input of the oxygen sensor 10, the inverting input of the operational amplifier 25 becomes more positive than the noninverting input. The output of the operational amplifier goes negative and with the diode 33 still blocked, it is the open circuit amplification of the operational amplifier that is effective. Thus, the very slightest increase of the output of the oxygen sensor 10 suffices to produce an output voltage change that corresponds to the threshold voltage of the diode 33. If the output voltage of the oxygen sensor 10 rises further, the output of the operational amplifier 25 becomes more strongly negative. The diode 33 then becomes conducting and the potential at the anode of the diode 33 is pulled down by the amplifier output. The feedback resistor 36, which determines the gain of the operational amplifier 25 will always draw away exactly enough current from the voltage divider formed by the resistors 26 and 28, in the region of amplification, to maintain a zero potential difference between the inverting and non-inverting inputs of the amplifier 25. Beginning at the voltage fixed by the voltage divider resistors 29 and 30, the output voltage of the oxygen sensor 10 will accordingly be linearly amplified.

The outputs of the three amplifiers 22, 23 and 24 are connected to a common point through the respective resistors 37, 38 and 39, this common point being the inverting input of an operational amplifier 40 that is connected as a summing amplifier. A sum voltage appears at the output of the operational amplifier unit 40 that can be so modified or regularized by the choice of the gain produced in the individual amplifiers 22, 23 and 24 and by the magnitude of the resistors 37, 38 and 39 that an unambiguous relation is established to the value of λ. The non-inverting input of the operational amplifier 40 is connected to the tap of a voltage divider constituted of the resistors 41 and 42 connected across the supply voltage between the positive voltage bus 27 and the grounded negative voltage bus 21. A resistor 43 is connected between the inverting input of the operational amplifier 40 and the positive voltage bus and a feedback resistor 44 is connected between the inverting input and the output of the operational amplifier 40. A resistor 45 is connected between the positive voltage bus 27 and the output of the operational amplifier 44. Finally, an indicating device 46 is connected with the output of the operational amplifier 40. The indicating device is also connected to the tap of a voltage divider constituted by the resistors 47 and 48. The scale of the indicating device 46 can conveniently be calibrated in values of λ, because the regularized output voltage appearing at the output of the operational amplifier 40 can provide a reasonable spread of the λ values over the range of indication. The Zener diode 49 connected between the positive voltage bus 27 and the negative voltage bus 21 serves to stabilize the supply voltage for the circuit just described.

The advantage of the circuit above described is that the output voltage of the oxygen sensor 10 that in itself is unsuitable for a direct evaluation in terms of the air number λ is so regularized by the amplifiers 22, 23 and 24 operating in different portions of the range of sensor output value, that even in the mid-portion of the characteristic curve shown in FIG. 2 it is possible to establish an unambiguous relation between the output signals of the oxygen sensor 10 and the air number λ. There is also the further advantage that by means of the temperature dependent resistor 28 provided in the input voltage divider of the operational amplifier 25, temperature dependent variations of the output signal of the oxygen sensor 10 can be compensated for.

If the oxygen sensor 10 is thermostatically heated by the heater 51 controlled by thermostat 52 and its temperature thus maintained at a constant value (e.g., 800° C), it is possible to dispense with any necessity of utilizing a negative temperature coefficient in the amplifier input such as the resistor 28 connected between the inverting input of the operational amplifier 25 and the terminal 16 of the oxygen sensor. The evaluation of the output signal of the oxygen sensor 10 is then limited to operation on a single exactly defined characteristic curve that can be evaluated in the manner shown and utilized to operate an indicator. It is also possible to counteract the irregularity of the characteristic curve in whole or in part by a non-linear subdivision of the scale of the indicator device, reducing the requirements imposed on the amplifier circuits. An indicating device with increased sensitivity in a part of the scale corresponding to the steep mid-portion of the characteristic curve of the sensor output can also be used to increase the accuracy of the measurement in the steep part of the characteristic curves 18 and 19.

The kind of regularizing carried out by means of the amplifiers 22, 23 and 24 in the illustrative embodiment of the invention described in connection with FIG. 3 can also be obtained with resistor-diode networks that are in themselves well known, but subject to the temperature sensitivity of diodes. A heater 51 controlled by a thermostat 52 shown for FIG. 3 to give the sensor 10 approximately the same temperature before it warms up as when it has reached normal engine temperature. A heat shield 53 around the sensor is also shown there. These, of course, are not necessary, but may be helpful in service. Thus it will be understood, in general, that although the invention has been described in detail with respect to a particular illustrative embodiment, some variations are possible within the inventive concept.

We claim:

1. Apparatus for continuously measuring the composition of a fuel-air mixture of an internal combustion engine by means of an oxygen sensor located in an exhaust duct of said engine, comprising:

an oxygen sensor (10) positioned so as to respond to the oxygen content of exhaust gas in said exhaust duct;

a plurality of amplifiers (22, 23, 24) with their inputs supplied in common with the output of said oxygen sensor (10), each of said amplifiers having a different value of gain and having a negative-feedback resistor path (36) and also having input voltage comparison means, with reference voltage provision, for setting a threshold input voltage, different for each amplifier, and diode means for blocking delivery of the amplifier output and rendering ineffective said feedback path when the input voltage does not exceed said threshold input voltage, said different threshold input voltages of the respective amplifiers having values defining intervals of input voltage range over which the response characteristic of said oxygen sensor has a different slope;

indicator means, and coupling means comprising coupling resistors for coupling the outputs of said amplifiers (22, 23, 24), so as to provide a common drive for said indicator means, whereby the indicator means is caused to represent the composition of the fuel-air mixture acting on said oxygen sensor.

2. Measuring apparatus as defined in claim 1, in which said coupling resistors are connected as summing resistors (37, 38, 39) of a summing circuit and the activating circuit of said indicating means (46) is connected to the output of said summing circuit.

3. Measuring apparatus as defined in claim 1, in which at least one component of said amplifiers (22, 23, 24) is a temperature dependent component for compensating the temperature characteristic of the output signal of said oxygen sensor (10).

4. Measuring apparatus as defined in claim 3, in which said temperature dependent component is a negative temperature coefficient resistor (28).

5. Measuring apparatus as defined in claim 3, in which said temperature dependent component (28) is located in the immediate neighborhood of said oxygen sensor (10).

6. Measuring apparatus as defined in claim 1, in which said oxygen sensor (10) is provided with means including a controlled heater, for maintaining said oxygen sensor at a constant temperature.

7. Measuring apparatus as defined in claim 1, in which said oxygen sensor is located in an exhaust pipe for response to the composition of exhaust gas of an engine, and in which said oxygen sensor is surrounded by a heat shield.

8. Measuring apparatus as defined in claim 1, in which each of said amplifiers comprises an operational amplifier (25) having its inverting input connected to the output voltage ($U_s$) of said oxygen sensor and having its non-inverting input connected to the tap of a voltage divider (29, 30) across the source of operating voltage of said operational amplifier, said operational amplifier further having a first semiconductor device (33) connected between the output of said operational amplifier and the tap of a second voltage divider (34, 35) across said source, and having a second semiconductor, which is a diode (32) connected between the output of the operational amplifier and the inverting input thereof, said negative feedback resistor path (36) connected between said tap of said second voltage divider and the inverting input of said operational amplifier.

9. Measuring device as defined in claim 8, provided with a second stage of amplification comprising a second stage operational amplifier (40) of which the inverting input is connected through adjustable resistors (37, 38, 39) respectively to the tap of said second voltage divider (34, 35) of each of the operational amplifiers (25) referred to in claim 8, so that said second stage operational amplifier (40) operates as a summing amplifier, at the output of which a voltage useful for controlling a fuel-injection system for said engine is produced.

* * * * *